(12) United States Patent
Violette et al.

(10) Patent No.: US 7,691,807 B2
(45) Date of Patent: *Apr. 6, 2010

(54) HYBRID OLIGOMERS, THEIR PREPARATION PROCESS AND PHARMACEUTICAL COMPOSITIONS CONTAINING THEM

(75) Inventors: Aude Violette, Schiltighen (FR); Jean-Paul Briand, Strasbourg (FR); Robert Zimmer, Mulhouse (FR); Gilles Guichard, Rue du Milieu (FR)

(73) Assignees: Centre National de la Recherche Scientifique (CNRS), Paris Cedex (FR); ImmuPharma France SA, Mulhouse Cedex (FR)

(*) Notice: Subject to any disclaimer, the term of this patent is extended or adjusted under 35 U.S.C. 154(b) by 0 days.

This patent is subject to a terminal disclaimer.

(21) Appl. No.: 11/378,050

(22) Filed: Mar. 17, 2006

(65) Prior Publication Data
US 2006/0211625 A1    Sep. 21, 2006

Related U.S. Application Data

(60) Provisional application No. 60/662,785, filed on Mar. 18, 2005.

(51) Int. Cl.
*A61K 38/00* (2006.01)
(52) U.S. Cl. .......................................................... 514/2
(58) Field of Classification Search ....................... None
See application file for complete search history.

(56) References Cited

U.S. PATENT DOCUMENTS

| | | | | |
|---|---|---|---|---|
| 5,595,756 | A | * | 1/1997 | Bally et al. ................... 424/450 |
| 7,060,845 | B2 | | 6/2006 | Guichard |
| 2005/0038105 | A1 | | 2/2005 | Guichard |

OTHER PUBLICATIONS

Tamilarasu et al. "Targeting RNA with peptidomimetic oligomers in human cells." Biorg. Med. Chem. Let., 2001, 11, 505-7.*
Boeijen & Liskamp "Solid-Phase Synthesis of Oligourea Peptidomimetics." Eur. J. Org. Chem., 1999, 2127-35.*
Burgess et al. "Solid Phase Synthesis of Oligoureas." J. Am. Chem. Soc., 1997, 119, 1556-64.*
Patch & Barron "Mimicry of bioactive peptides via non-natural, sequence-specific peptidomimetic oligomers." Curr. Op. Chem. Bio., 2002, 6, 872-877.*
Hamuro et al. "De Novo Design of Antibacterial B-Peptides." J. Am. Chem. Soc., 1999, 121, 12200-1.*
Lui et al. "De Novo Design, Synthesis, and Characterization of Antimicrobial B-Peptides." J. Am. Chem. Soc., 2001, 123, 7553-9.*
Arvidsson et al. "On the antimicrobial and hemolytic activities of amphiphilic beta-peptides." ChemBioChem, 2001, 2, 771-3.*
Porter et al. "Non-haemolytic beta-amino-acid oligomers." Nature, 2000, 404, 565.*
Porter et al. "Mimicry of host-defense peptides by unnatural oligomers: antimicrobial beta-peptides." J. Am. Chem. Soc., 2002, 124, 7324-30.*
LePlae et al. "Tolerance of acyclic residues in the beta-peptide 12-helix: access to diverse side-chain arrays for biological applications." J. Am. Chem. Soc., 2002, 124, 6820-1.*
Coward J.K., N-Me-pAB-Glu-gamma-Glu-gamma-Tyr(3-NO2): An internally quenched fluorogenic gamma-glutamyl hudrolase substrate. Bioorganic & Medicinal Chemistry Letters, Oxford GB, vi 1(12): 1561-1564 (2001).*
Semetey et al, Stable Helical Secondary Structure in Short-Chain N,N'-Linked Oligourea Bearing Proteinogenic Side Chains, Angew Chem Int Ed (2002) vol. 41, pp. 1893-1895.*
Gao, Yi et, al., "Theoretical study of the secondary structures of unionized poly(y-D-glutamic acid)," Molecular Physics (2004), 102(23-24).*
Sporn et at, "Chemoprevention of Cancer," Carcinogenesis, vol. 21 (2000), 525-530.*
Gura, "Cancer Models: Systems for Identifying New Drugs Are Often Faulty," Science vol. 278 (1997), 1041-1042 provided as HTML file pp. 1-5.*
Tamilarasu, N. "High Affinity and Specific Binding of HIV-1 Tar RNA by a Tat-Derived Oligourea," Journal of the American Chemical Society (1999), 121(7), 1597-1598.*
Tamilarasu, N. "Supporting Information -High Affinity and Specific Binding of HIV-1 TAR RNA by a Tat-Derived Oligourea," Journal of the American Chemical Society (1999), 121(7), pp. S1 -S12.*
Burgess K. et al., Solid phase synthesis of Oligoureas. J. Of American Chem. Soc. v119(7): 1556-1564 (1997) from Applicant's IDS.*
Coward J.K. N-Me-pAB-Glu-gamma-Glu-gamma-Tyr(3-NO2): An internally quenched fluorogenic gamma-glutamyl hudrolase substrate. Bioorganic & Medicinal Chemistry Letters, Oxford GB, v11(12): 1561-1564 (2001).
Hintermann T., et al., Gamma-peptides forming more stable secondary structures than alpha-peptides: synthesis and helical NMR-solution structure of the hexapeptide analog of H-(Val-Ala-Leu)2-0H. Helvetica Chimica Acta., v81: 983-1002 (1998).
Hemmerlin C. et al., Helix-forming oligoureas: temperature-dependent NMR, structure determination, and circular dichroism of a nonamer with functionalized side chains. v85(11): 3692-3711 (2002).

* cited by examiner

*Primary Examiner*—Cecilia Tsang
*Assistant Examiner*—Thomas S Heard
(74) *Attorney, Agent, or Firm*—McCarter & English, LLP

(57) ABSTRACT

The present invention relates to compositions and methods for producing therapeutic oligomeric compounds. In one aspect the invention relates to methods for administering the oligomeric compounds for the treatment and prevention of disease, for example, a fungal infection, bacterial infection, or cancer, in a mammal. In particular, the invention relates to medicaments comprising various novel oligomeric compounds and pharmaceutically acceptable salts thereof. The compounds of the invention may optionally be administered with at least one of a pharmaceutically acceptable excipient, pharmacologically active agent or a combination thereof.

28 Claims, No Drawings

HYBRID OLIGOMERS, THEIR PREPARATION PROCESS AND PHARMACEUTICAL COMPOSITIONS CONTAINING THEM

REFERENCE TO RELATED APPLICATION

Under 35 U.S.C. §119(e) this application claims the benefit of U.S. Provisional Application No. 60/662,785 filed Mar. 18, 2005, which is hereby incorporated by reference in its entirety.

FIELD OF THE INVENTION

The present invention relates to compositions and methods for the treatment and prevention of disease in a mammal. In particular, the invention relates to medicaments comprising various novel oligomeric compounds and pharmaceutically acceptable salts thereof.

The compounds of the invention may optionally be administered with at least one of a pharmaceutically acceptable excipient, pharmacologically active agent or a combination thereof.

BACKGROUND OF THE INVENTION

The 1950s-1970s saw the discovery of multiple classes of antibiotics, and their development into drugs changed a simple bacterial infection from life threatening to trivial. This golden age of antibiotics engendered such optimism that it was commonly thought bacterial infections would be rapidly eliminated as a cause of mortality. Unfortunately, bacterial resistance to all classes of antibiotics soon appeared. Now, three decades after the end of this era, drug-resistant bacteria are ubiquitous in hospital settings and annually 90000 people die of such infections each year in the US alone. One quarter of the bacteria that most frequently cause hospital-acquired infections are resistant to the preferred antibiotic treatment, and an alarming 70% of hospital acquired infections are resistant to at least one antibiotic.

Methicillin-resistant *Staphylococcus aureus* (MRSA) is the most common drug-resistant bacteria in hospitals, accounting for greater than 30% of all nosocomial infections. MRSA can also be community-acquired, causing severe illness and even death. Furthermore, the incidence of extended spectrum-lactamase (ESBL) production in clinical *Klebsiella* isolates has increased steadily in the past several years, severely curtailing the effectiveness of lactam antibiotics. Perhaps most disturbing is the recent estimation that one third of enterococci in intensive care units are resistant to vancomycin, often viewed as the antibiotic of last resort.

The list of drug-resistant pathogens is extensive and growing. These bacterial infections are of particular concern in elderly, infirm, or immuno-compromised patients. Individuals with tuberculosis, AIDS, salmonellosis, gonorrhea, or malaria who contract drug-resistant bacterial infections experience longer hospital stays and have mortality rates more than twice as high as those with antimicrobial-susceptible infections. Thus, resistant bacteria not only complicate medical treatment, but also add billions of dollars to medical costs every year.

The problem of bacterial resistance to antibiotics is exacerbated by the downward trend in antibacterial discovery and development. There has been a 56% decrease over the last two decades in the annual number of antibiotics approved by the FDA. In fact, only six antibiotics produced by large pharmaceutical companies are currently in late stage clinical trials, and all of these are derivatives of known antibiotics. Although the reasons for the halting of many antibacterial programs at major pharmaceutical companies are myriad, the acute (not chronic) nature of most bacterial infections and the public expectation for no side effects has made antibacterial research less profitable and more difficult when compared to other disease areas.

The research activity in this area has mainly concentrated on the design and in vitro studies of amphiphilic helical beta-peptides with antimicrobial activity. In view of their high propensity for helical conformations as well as their resistance to proteolytic degradation, beta-peptides represent promising antibacterial candidates.

Antimicrobial α-peptides that adopt cationic amphipatic α-helical structures upon binding to cell membranes (e.g., mellitin from bee venom, magainins from frog skin, cecropins from porcine small intestine) are ubiquitous in nature (Antimicrobial Sequences Database, http://www.bbcm.units.it/~tossi/pag1.htm) and represent important effectors molecules of innate immunity. These peptides generally cause cell death by a two step mechanism involving interaction with the lipid component of the membrane (while in bacteria the outer leaflet of the membrane is essentially composed of lipids with negatively charged phospholipid headgroups, it is almost neutral in plants and animals) followed by membrane permeabilization. Several mechanisms for membrane permeabilization have been postulated including transient pore formation ("barrel-stave model) or detergent-like disruption of the membrane ("carpet model"). The lytic activity of amphiphilic antimicrobial peptides is strongly influenced by properties such as helix stability, amphiphilicity (hydrophobic moment), hydrophobicity, relative width of the hydrophilic and hydrophobic faces of the helix as well as net charge. Despite many structure-activity studies, lead optimization remains challenging because sequence modifications of α-peptides generally affect several parameters at the same time. In addition, low activity on human cell membranes is a prerequisite for a cell-lytic peptide to be of therapeutic value and de-novo design of helical membrane-lytic peptides with high membrane selectivity necessitates an even finer tuning between these five different parameters.

Both the $3_{14}$ and $2.5_{12}$ helical backbones have been found suitable for the design of antimicrobial β-peptides. In order to cluster polar residues on one face of the helix, amphiphilic $3_{14}$-helical β-peptides have been constructed from hydrophobic-cationic-hydrophobic- or hydrophobic-hydrophobic-cationic residue triads.

Some β3-nonapeptides with a C-terminal amide were found to be active against Gram-Positive (*S. Aureus* and *E. Faecium* strains were clinical isolates resistant to penicillin and vancomycin, respectively) and Gram-negative bacteria with MIC values (in the range 1.6-12.5 mg/mL) comparable to that of the antimicrobial α-peptides mellittin and [Ala8,13,18]-magainin II amide (a highly potent synthetic analogue of natural magainin II). Although some of these compounds show no helix formation in water, they generally display a maximimum helicity in 40% aqueous TFE, a solvent system which is also known to promote helicity of amphiphilic α-peptides.

SUMMARY OF THE INVENTION

The present invention relates to compounds and methods for synthesizing compounds that are efficacious for the treatment and/or prevention of disease in a mammal, for example a human. In another aspect the invention relates to compounds useful in the treatment and/or prevention of microbial or bacterial infections and related diseases.

In one aspect, the invention relates to novel oligomeric compounds synthesized using the methods of the invention The invention also relates to pharmaceutical compositions comprising effective amounts of said compounds. In other aspects, the invention relates to therapeutic methods comprising the administration of an effective amount of the compounds of the invention to a mammal in need thereof.

In one aspect the present invention relates to oligomeric compounds and methods for synthesizing novel oligomeric compounds of the formula I:

$$X\text{-}[D^t]_n\text{-}Y \quad (I)$$

wherein n is an integer varying from 1 to 10;

t is an integer varying from 1 to n;

D is selected independently from members of the group consisting of moieties of the formula II:

$$(A^p)_i\text{-}(B^q)_j\text{-}(C^r)_k \quad (II)$$

wherein i, j, and k are independently selected integers from 0 to 10; and wherein the sum of i+j+k equals an integer of at least 2, and the sum of i+k equals an integer of at least 1;

p is an integer from 1 to i;

q is an integer from 1 to j;

r is an integer from 1 to k;

A is selected independently from members of the group consisting of moieties of the formula III:

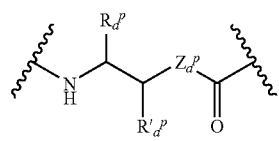

wherein $R_\alpha$ and $R'_\alpha$ are independently selected from the group consisting of a hydrogen atom, an amino acid side chain, a (C1-C10) alkyl, (C1-C10) alkenyl, (C1-C10) alkynyl, (C5-C12) monocyclic or bicyclic aryl, (C5-C14) monocyclic or bicyclic aralkyl, (C5-C14) monocyclic or bicyclic heteroalkyl and (C1-C10) monocyclic or bicyclic heteroaryl group comprising up to 5 heteroatoms selected from N, O, and S, said groups being able to be non-substituted or substituted by 1 to 6 substituents further selected from the group consisting of: a halogen atom, an $NO_2$, OH, amidine, benzamidine, imidazole, alkoxy, (C1-C4) alkyl, NH2, CN, trihalomethyl, (C1-C4) acyloxy, (C1-C4) monoalkylamino, (C1-C4) dialkylamino, guanidino group, bis alkylated or bis acylated guanido group;

$Z_a$ is NH, $CH_2$, or O;

B is a member selected from the group consisting of an alpha, beta or gamma amino acid residue;

C is selected independently from members of the group consisting of moieties of the formula IV:

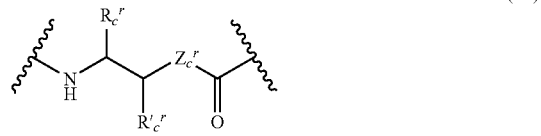

wherein $R_c$ and $R'_c$ are independently selected from the same group as $R_\alpha$ and $R'_\alpha$;

$Z_c$ is NH, $CH_2$, or O;

X is selected from the group consisting of a hydrogen atom, a biotinyl group, a cysteine residue, an $R_\alpha CO$, $R_\alpha OCO$, $R_\alpha NHCO$, $R_\alpha SO_2$, or $R_\alpha NHCS$;

wherein $R_\alpha$ is selected from the group consisting of fluorescein or a (C1-C6) pyridyldithioalkyl, (C1-C6) nitropyridyldithioalkyl, (C1-C10) alkyl, (C1-C10) alkenyl, (C1-C10) alkynyl, (C5-C12) aryl, (C5-C14) aralkyl, (C1-C5) heteroaryl group, said groups being able to be non-substituted or substituted by 1 to 6 substituents chosen from: a halogen atom, an $NO_2$, OH, (C1-C4) alkyl, $NH_2$, CN, trihalomethyl, (C1-C4) acyloxy, (C1-C4) dialkylamino, guanidino group, an SH group, a maleimide group;

Y represents $NH_2$, or a group chosen among the following: $NHR_\beta$, $OR_\beta$, and $NR_\beta R_\gamma$ group, $R\beta$ and $R_\gamma$ having the meaning given previously for $R_\alpha$; and wherein when j=0, at least one of the groups A is a group of formula (III) wherein $Z_a=CH_2$, or at least one of the groups C is a group of formula (IV) wherein $Z_c=CH_2$.

In an embodiment, when i+k=1 in the above-mentioned formula (V), j is greater than or equal to 1.

In any of the preferred embodiments, the present invention includes the free base or acid forms, as well as salts thereof, of the oligomeric compounds described by the above formula. The invention also includes the optical isomers, analogs, and derivatives of the compounds described by the above formula. In a further embodiment of the invention, mixtures of enantiomers and/or diastereoisomers, resulting from a single preparative step, combination, or interconversion are encompassed. In yet a further embodiment of the invention, the compounds described by the formula I are included in a pharmaceutically acceptable form, and optionally include at least one other ingredient, for example a suitable carrier, excipient, another pharmaceutically active ingredient or a combination thereof.

The invention also provides prodrug forms of the above described oligomeric compounds, wherein the prodrug is metabolized in vivo to produce an analog or derivative as set forth above. Indeed, some of the described compounds may be a prodrug for another analog or derivative. The term "prodrug" is well understood in the art and includes compounds that are converted to pharmaceutically active compounds of the invention in a mammalian system. For example, see *Remington's Pharmaceutical Sciences,* 1980, vol. 16, Mack Publishing Company, Easton, Pa., 61 and 424.

In another aspect of the invention, compositions containing the above described compounds are provided. Preferably, the compositions are formulated to be suitable for pharmaceutical or agricultural use by the inclusion of appropriate carriers or excipients.

In still another aspect of the invention, methods are provided for the administration of a suitable amount of a pharmaceutically acceptable form of the compounds described herein, to a mammal in need thereof, for example a human, for the treatment and/or prevention of a disease. In one of the embodiments, the invention comprises methods for the administration of a suitable amount of a pharmaceutically acceptable form of the compounds described herein, to a mammal in need thereof, for the treatment and/or prevention of microbial or bacterial infections and related diseases.

Additional advantageous features and functionalities associated with the systems, methods and processes of the present invention will be apparent from the detailed description which follows.

DETAILED DESCRIPTION OF THE INVENTION

When describing the compounds, compositions and methods of the invention, the following terms have the following meanings, unless otherwise indicated.

"Pharmaceutically acceptable salt" means those salts which retain the biological effectiveness and properties of the parent compounds and which are not biologically or otherwise harmful as the dosage administered. The compounds of this invention are capable of forming both acid and base salts by virtue of the presence of amino and carboxy groups respectively. Pharmaceutically acceptable base addition salts may be prepared from inorganic and organic bases. Salts derived from inorganic bases include, but are not limited to, the sodium, potassium, lithium, ammonium, calcium, and magnesium salts. Salts derived from organic bases include, but are not limited to, salts of primary, secondary and tertiary amines, substituted amines including naturally-occurring substituted amines, and cyclic amines, including isopropylamine, trimethyl amine, diethylamine, triethylamine, tripropylamine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, and N-ethylpiperidine. It should also be understood that other carboxylic acid derivatives would be useful in the practice of this invention, for example carboxylic acid amides, including carboxamides, lower alkyl carboxamides, di(lower alkyl)carboxamides, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

The term "treatment" as used herein includes any treatment of a condition or disease in an animal, particularly a mammal, more particularly a human, and includes: (i) preventing the disease or condition from occurring in a subject which may be predisposed to the disease but has not yet been diagnosed as having it; (ii) inhibiting the disease or condition, i.e. arresting its development; relieving the disease or condition, i.e. causing regression of the condition; or relieving the conditions caused by the disease, i.e. symptoms of the disease.

The term "therapeutically effective amount" refers to that amount which is sufficient to effect treatment, as defined herein, when administered to a mammal in need of such treatment. The therapeutically effective amount will vary depending on the subject and disease state being treated, the severity of the affliction and the manner of administration, and may be determined routinely by one of ordinary skill in the art.

"Heterocycle" refers to a heterocyclic group having from 4 to 9 carbon atoms and at least one heteroatom selected from the group consisting of N, O or S.

"Alkyl" refers to a branched or unbranched alkyl group having 1-6 carbon atoms, a branched or unbranched alkenyl group having 1-6 carbon atoms, a branched or unbranched alkinyl group having 1-6 carbon atoms.

"Hydroxyl" refers the functional group —OH when it is a substituent in an organic compound.

"Heterocyclic groups" can be optionally substituted with 1 to 5, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO2-alkyl, —SO2-substituted alkyl, —SO2-aryl, oxo (=O), and —SO2-heteroaryl. Such heterocyclic groups can have a single ring or multiple condensed rings. Preferred heterocyclics include morpholino, piperidinyl, and the like.

Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles.

The term "thiol" refers to the group —SH.

The term "thioalkoxy" refers to the group —S-alkyl.

"Amino acid" refers to any molecule that contains both amino and carboxylic acid functional groups, and includes any of the naturally occurring amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D, L, or DL form. The side chains of naturally occurring amino acids are well known in the art and include, for example, hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), alkaryl (e.g., as in phenylalanine and tryptophan), substituted arylalkyl (e.g., as in tyrosine), and heteroarylalkyl (e.g., as in histidine).

"Amidine" refers to a functional group that has two amine groups attached to the same carbon atom with one carbon-nitrogen double bond: HN=CR'—NH"2.

"Alkoxyl" refers to an alkyl group linked to oxygen thus: R—O—, where R is an alkyl.

"Substituted alkyl" refers to a branched or unbranched alkyl, alkenyl or alkinyl group having 1-10 carbon atoms and having substituted by one or more substituents selected from the group consisting of hydroxyl, mercapto, carbylmercapto, halogen, carbyloxy, amino, amido, carboxyl, cycloalkyl, sulfo or acyl. These substituent generic groups having the meanings being identical with the definitions of the corresponding groups as defined herein.

"Halogen" refers to fluorine, bromine, chlorine, and iodine atoms.

"Acyl" denotes the group —C(O)R$_e$, where R$_e$ is hydrogen, alkyl, substituted alkyl, aryl, substituted aryl, arylalkyl, substituted arylalkyl, cycloalkyl, substituted cycloalkyl whereas these generic groups have meanings which are identical with definitions of the corresponding groups as defined in this legend.

"Acloxy" denotes the group —OAc, where Ac is an acyl, substituted acyl, heteroacyl or substituted heteroacyl whereas these generic groups have meanings which are identical with definitions of the corresponding groups as defined in this legend.

"Alkylamino" denotes the group —NR$_f$R$_g$, where R$_f$ and R$_g$, that are independent of one another, represent hydrogen, alkyl, substituted alkyl, aryl, substituted aryl, heteroaryl or substituted heteroaryl, whereas these generic substituents have meanings which are identical with definitions of the corresponding groups defined herein.

"Aryl" refers to an aromatic carbocyclic group having from 1 to 18 carbon atoms and being composed of at least one aromatic or multiple condensed rings in which at least one of which being aromatic.

"Substituted aryl" refers to an aromatic carbocyclic group having from 1 to 18 carbon atoms and being composed of at least one aromatic ring or of multiple condensed rings at least one of which being aromatic. The ring(s) are optionally substituted with one or more substituents selected from the group consisting of halogen, alkyl, hydroxyl, carbylmercapto, alkylamino, carbyloxy, amino, amido, carboxyl, nitro, mercapto or sulfo, whereas these generic substituent group have meanings which are identical with definitions of the corresponding groups as defined in this legend.

"Heteroaryl" refers to a heterocyclic group having from 4 to 9 carbon atoms and at least one heteroatom selected from the group consisting of N, O or S with at least one ring of this group being aromatic.

"Substituted heteroaryl" refers to a heterocyclic group having from 4 to 9 carbon atoms and at least one heteroatom selected from the group consisting of N, O or S with at least one ring of this group being aromatic and this group being substituted with one or more substituents selected from the group consisting of halogen, alkyl, carbyloxy, carbylmercapto, alkylamino, amido, carboxyl, hydroxyl, nitro, mercapto or sulfo, whereas these generic substituent group have meanings which are identical with definitions of the corresponding groups as defined in this legend.

"Carboxyl" denotes the group —C(O)OR, where R is hydrogen, alkyl, substituted alkyl, aryl, substituted aryl, heteroaryl or substituted heteroaryl, whereas these generic substituents have meanings which are identical with definitions of the corresponding groups defined herein.

"Cycloalkyl" refers to a monocyclic or polycyclic alkyl group containing 3 to 15 carbon atoms.

"Substituted cycloalkyl" refers to a monocyclic or polycyclic alkyl group containing 3 to 15 carbon atoms and being substituted by one or more substituents selected from the group consisting of halogen, alkyl, substituted alkyl, carbyloxy, carbylmercapto, aryl, nitro, mercapto or sulfo, whereas these generic substituent groups have meanings which are identical with definitions of the corresponding groups as defined in this legend.

"Heterocycloalkyl" refers to a monocyclic or polycyclic alkyl group containing 3 to 15 carbon atoms which at least one ring carbon atom of its cyclic structure being replaced with a heteroatom selected from the group consisting of N, O, S or P.

"Substituted heterocycloalkyl" refers to a monocyclic or polycyclic alkyl group containing 3 to 15 carbon atoms which at least one ring carbon atom of its cyclic structure being replaced with a heteroatom selected from the group consisting of N, O, S or P and the group is containing one or more substituents selected from the group consisting of halogen, alkyl, substituted alkyl, carbyloxy, carbylmercapto, aryl, nitro, mercapto or sulfo, whereas these generic substituent group have meanings which are identical with definitions of the corresponding groups as defined in this legend.

The term "aryl" refers to an unsaturated aromatic carbocyclic group of from 6 to 20 carbon atoms having a single ring (e.g., phenyl) or multiple condensed (fused) rings, wherein at least one ring is aromatic (e.g., naphthyl, dihydrophenanthrenyl, fluorenyl, or anthryl). Preferred aryls include phenyl, naphthyl and the like.

The term "alkenyl" refers to a monoradical of a branched or unbranched unsaturated hydrocarbon group preferably having from 2 to 40 carbon atoms, more preferably 2 to 10 carbon atoms and even more preferably 2 to 6 carbon atoms. Preferred alkenyl groups include ethenyl (—CH=CH2), n-propenyl (—CH2CH=CH2), iso-propenyl (—C(CH3)=CH2), and the like.

"Imidazole" refers to a heterocyclic base of the general formula: $C_3H_4N_2$.

"Aralkyl group" refers to, for example, a C1-C6 alkyl group which is attached to 1 or 2 aromatic hydrocarbon rings having from 6 to 10 carbon atoms and which has a total of 7 to 14 carbon atoms, such as the benzyl, alpha-naphthylmethyl, indenylmethyl, diphenylmethyl, 2-phenethyl, 2-alpha-naphthylethyl, 3-phenylpropyl, 3-alpha-naphthylpropyl, phenylbutyl, 4-alpha-naphthylbutyl or 5-phenylpentyl groups.

"Guanidine" refers generally to the amidine of amidocarbonic acid and has the general formula of: $C(NH_2)_3$.

The terms "aralkyl" and "heteroarylalkyl" refer to groups that comprise both aryl or, respectively, heteroaryl as well as alkyl and/or heteroalkyl and/or carbocyclic and/or heterocycloalkyl ring systems according to the above definitions.

The intermediates and the desired compounds in the processes described can be isolated and purified by purification methods conventionally used in organic synthetic chemistry, for example, neutralization, filtration, extraction, washing, drying, concentration, recrystallization, and various kinds of chromatography. The intermediates may be subjected to the subsequent reaction without purification.

In one embodiment the present invention relates to oligomeric compounds and methods for synthesizing novel oligomeric compounds of the formula I:

X-[D$^t$]$_n$-Y    (I)

wherein n is an integer varying from 1 to 10;

t is an integer varying from 1 to n;

D is selected independently from members of the group consisting of moieties of the formula II:

(A$^p$)$_i$-(B$^q$)$_j$-(C$^r$)$_k$    (II)

wherein i, j, and k are independently selected integers from 0 to 10; and wherein the sum of i+j+k equals an integer of at least 2, and the sum of i+k equals an integer of at least 1;

p is an integer from 1 to i;

q is an integer from 1 to j;

r is an integer from 1 to k;

A is selected independently from members of the group consisting of moieties of the formula III:

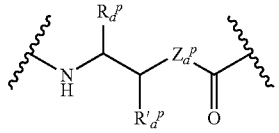

(III)

wherein $R_\alpha$ and $R'_\alpha$ are independently selected from the group consisting of a hydrogen atom, an amino acid side chain, a (C1-C10) alkyl, (C1-C10) alkenyl, (C1-C10) alkynyl, (C5-C12) monocyclic or bicyclic aryl, (C5-C14) monocyclic or bicyclic aralkyl, (C5-C14) monocyclic or bicyclic heteroalkyl and (C1-C10) monocyclic or bicyclic heteroaryl group comprising up to 5 heteroatoms selected from N, O, and S, said groups being able to be non-substituted or substituted by 1 to 6 substituents further selected from the group consisting of: a halogen atom, an $NO_2$, OH, amidine, benzamidine, imidazole, alkoxy, (C1-C4) alkyl, NH2, CN, trihalomethyl, (C1-C4) acyloxy, (C1-C4) monoalkylamino, (C1-C4) dialkylamino, guanidino group, bis alkylated or bis acylated guanido group;

$Z_a$ is NH, $CH_2$, or O;

B is a member selected from the group consisting of an alpha, beta or gamma amino acid residue;

C is selected independently from members of the group consisting of moieties of the formula IV:

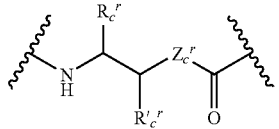

(IV)

wherein $R_c$ and $R'_c$ are independently selected from the same group as $R_\alpha$ and $R'_\alpha$;

$Z_c$ is NH, $CH_2$, or O;

X is selected from the group consisting of a hydrogen atom, a biotinyl group, a cysteine residue, an $R_\alpha CO$, $R_\alpha OCO$, $R_\alpha NHCO$, $R_\alpha SO_2$, or $R_\alpha NHCS$;

wherein $R_\alpha$ is selected from the group consisting of fluorescein or a (C1-C6) pyridyldithioalkyl, (C1-C6) nitropyridyldithioalkyl, (C1-C10) alkyl, (C1-C10) alkenyl, (C1-C10) alkynyl, (C5-C12) aryl, (C5-C14) aralkyl, (C1-C5) heteroaryl group, said groups being able to be non-substituted or substituted by 1 to 6 substituents chosen from: a halogen atom, an $NO_2$, OH, (C1-C4) alkyl, $NH_2$, CN, trihalomethyl, (C1-C4) acyloxy, (C1-C4) dialkylamino, guanidino group, an SH group, a maleimide group;

Y represents $NH_2$, or a group chosen among the following: $NHR_\beta$, $OR_\beta$, and $NR_\beta R_\gamma$ group, $R_\beta$ and $R_\gamma$ having the meaning given previously for $R_\alpha$; and wherein when j=0, at least one of the groups A is a group of formula (III) wherein $Z_a = CH_2$, or at least one of the groups C is a group of formula (IV) wherein $Z_c = CH_2$.

The present invention covers all possible isomers including tautomers and mixtures thereof. Where chiral carbons lend themselves to two different enantiomers, both enantiomers are contemplated as well as procedures for separating the two enantiomers.

In the case where a salt of a compound is desired and the compound is produced in the form of the desired salt, it can be subjected to purification as such. In the case where a compound is produced in the free state and its salt is desired, the compound is dissolved or suspended in a suitable organic solvent, followed by addition of an acid or a base to form a salt.

The present invention also relates to pharmaceutically acceptable salts, racemates, and optical isomers thereof of formula I. The compounds of this invention typically contain one or more chiral centers. Accordingly, this invention is intended to include racemic mixtures, diasteromers, enantiomers and mixture enriched in one or more steroisomer. The scope of the invention as described and claimed encompasses the racemic forms of the compounds as well as the individual enantiomers and non-racemic mixtures thereof.

In a further aspect of the invention, methods for the use of the above described analogs and derivatives, as well as compositions, are provided. These methods include uses of the invention's compounds to treat human and agricultural diseases and conditions. Examples of human diseases and conditions include, but are not limited to, inflammation, tissue transplantation, cancerous diseases, malaria, African sleeping sickness, Chagas disease, toxoplasmosis, psoriasis, restenosis, treatment of peptic ulcer, glaucoma, IBD, Crohn's disease and other inflammatory bowel diseases, fungal, bacterial, microbial, viral, and parasitic diseases.

"Bacterial diseases" as used herein, refers to infections caused by bacteria and includes, for example, the following: *Legionella*, bacterium associated with legionellosis; *Escherichia coli* O157:H7: discovered in 1982, this bacterium which is normally transmitted by means of contaminated food, has been at the origin of attacks of hemolytic and uremic syndromes; *Borrelia burgdorferi*: detected in the United States in 1982, it has been identified as being the cause of Lyme's disease; *Vibrio cholerae* O139: new strain associated with an epidemic cholera; *Helicobacter pyroli*: bacterium associated with a gastro-intestinal ulcer. The infections associated with bacteria which are becoming resistant to more and more extensive range of antibiotics are also designated. Thus, in numerous regions, the antibiotics of first intention, which are inexpensive, have lost their effectiveness against the infections linked to the following bacteria: *Bacillus anthracis, Escherichia coli, Streptococcus pneumoniae, Enterococcus faecalis, Mycobacterium tuberculosis, Pseudomonas aeruginosa, Neisseria gonorrhoca, Pneumococcus, Shigella, Staphylococcus aureus* (associated with a *staphylococcic* toxic shock) and *Moraxella catarrhalis*.

According to any of the embodiments of the present invention, the bacterial infections to be treated by the compounds of the invention include, for example, *Salmonella typhi, Shigella dysenteria, Pseudomonas cepacia, Bacillus cereus, Salmonella, Clostridium perfringens, Campylobacter, Listeria monocytogenes, Vibrio parahaemolyticus, Clostridium botulinum, Variola major, Francisella tularensis, Yersinia pestis*, a multiply drug resistant strain of *Staphylococcus aureus* or a vancomycin-resistant strain of *Enterococcus faecalis*.

By "fungal diseases", is designated the infections caused by pathogenic fungi including, for example, *Candida albicans*, associated with candidosis, *Aspergillus nidulans, Aspergillus parasiticus*, associated with aspergillosis, and *Neurospora crassa*. The fungal diseases include the diseases caused by pathogenic fungi, in particular those of the family of fungi imperfecti, in particular the moniliales or also those of the family of the hyprocreales or of that of the sphaeriales.

By "cancerous diseases", is designated in particular cancers, and in particular tumours of the digestive system (liver, intestine, esophagus, pancreas etc.), the urogenital system (uterus, prostate, kidney, bladder etc.), the endocrine glands, the eye, the skin, the breast, the bone, the nervous system, the thorax (lung etc.).

Therapeutic Administration

Another of the preferred embodiments of the present invention includes therapeutic compositions comprising the compounds of the invention in a pharmaceutically acceptable form. In still another of the preferred embodiments, the present invention includes methods for the treatment and/or prevention of disease in a mammal, for example, a human, comprising administering of an effective amount of a compound of the invention in a pharmaceutically acceptable form. The compound of the invention may optionally be administered together with at least one of a carrier, an excipient, another biologically active agent or any combination thereof.

Suitable routes for administration include oral, peroral, rectal, vassal, topical (including ocular, buccal and sublingual), vaginal and parental (including subcutaneous, intramuscular, intravitreous, intravenous, intradermal, intrathecal and epidural). The preferred route of administration will depend upon the condition of the patient, the toxicity of the compound and the site of infection, among other considerations known to the clinician.

The therapeutic composition of the invention comprises about 1% to about 95% of the active ingredient, single-dose forms of administration preferably comprising about 20% to about 90% of the active ingredient and administration forms which are not single-dose preferably comprising about 5% to about 20% of the active ingredient. Unit dose forms are, for example, coated tablets, tablets, ampoules, vials, suppositories or capsules. Other forms of administration are, for example, ointments, creams, pastes, foams, tinctures, lipsticks, drops, sprays, dispersions and the like. Examples are capsules containing from about 0.05 g to about 1.0 g of the active ingredient.

The pharmaceutical compositions of the present invention are prepared in a manner known per se, for example by means of convential mixing, granulating, coating, dissolving or lyophilizing processes.

Preferably, solutions of the active ingredient, and in addition also suspensions or dispersions, especially isotonic aqueous solutions, dispersions or suspensions, are used, it being possible for these to be prepared before use, for example in the case of lyophilized compositions which comprise the active substance by itself or together with a carrier, for example mannitol. The pharmaceutical compositions can be sterilized and/or comprise excipients, for example preservatives, stabilizers, wetting agents and/or emulsifiers, solubilizing agents, salts for regulating the osmotic pressure and/or buffers, and they are prepared in a manner known per se, for example by means of convential dissolving or lyophilizing processes. The solutions or suspensions mentioned can comprise viscosity-increasing substances, such as sodium carboxymethylcellulose, carboxymethylcellulose, dextran, polyvinylpyrrolidone or gelatin.

Pharmaceutically acceptable forms include, for example, a gel, lotion, spray, powder, pill, tablet, controlled release tablet, sustained release tablet, rate controlling release tablet, enteric coating, emulsion, liquid, salts, pastes, jellies, aerosols, ointments, capsules, gel caps, or any other suitable form that will be obvious to one of ordinary skill in the art.

Suspensions in oil comprise, as the oily component, the vegetable, synthetic or semi-synthetic oils customary for injection purposes. Oils which may be mentioned are, in particular, liquid fatty acid esters which contain, as the acid component, a long-chain fatty acid having 8-22, in particular 12-22, carbon atoms, for example lauric acid, tridecylic acid, myristic acid, pentadecylic acid, palmitic acid, margaric acid, stearic acid, arachidinic acid, behenic acid or corresponding unsaturated acids, for example oleic acid, elaidic acid, euric acid, brasidic acid or linoleic acid, if appropriate with the addition of antioxidants, for example vitamin E, beta.-carotene or 3,5-di-tert-butyl-4-hydroxytoluene. The alcohol component of these fatty acid esters has not more than 6 carbon atoms and is mono- or polyhydric, for example mono-, di- or trihydric alcohol, for example methanol, ethanol, propanol, butanol, or pentanol, or isomers thereof, but in particular glycol and glycerol. Fatty acid esters are therefore, for example: ethyl oleate, isopropyl myristate, isopropyl palmitate, "Labrafil M 2375" (polyoxyethylene glycerol trioleate from Gattefosee, Paris), "Labrafil M 1944 CS" (unsaturated polyglycolated glycerides prepared by an alcoholysis of apricot kernel oil and made up of glycerides and polyethylene glycol esters; from Gattefosee, Paris), "Labrasol" (saturated polyglycolated glycerides prepared by an alcoholysis of TCM and made up of glycerides and polyethylene glycol esters; from Gattefosee, Paris) and/or "Miglyol 812" (triglyceride of saturated fatty acids of chain length $C_8$ to $C_{12}$ from Huls AG, Germany), and in particular vegetable oils, such as cottonseed oil, almond oil, olive oil, castor oil, sesame oil, soybean oil and, in particular, groundnut oil.

The preparation of the injection compositions is carried out in the customary manner under sterile conditions, as are bottling, for example in ampoules or vials, and closing of the containers.

For example, pharmaceutical compositions for oral use can be obtained by combining the active ingredient with one or more solid carriers, if appropriate granulating the resulting mixture, and, if desired, processing the mixture or granules to tablets or coated tablet cores, if appropriate by addition of additional excipients.

Suitable carriers are, in particular, fillers, such as sugars, for example lactose, sucrose, mannitol or sorbitol cellulose preparations and/or calcium phosphates, for example tricalcium phosphate, or calcium hydrogen phosphate, and furthermore binders, such as starches, for example maize, wheat, rice or potato starch, methylcellulose, hydroxypropylmethylcellulose, sodium carboxymethylcellulose and/or polyvinylpyrrolidine, and/or, if desired, desintegrators, such as the above mentioned starches, and furthermore carboxymethylstarch, cross-linked polyvinylpyrrolidone, alginic acid or a salt thereof, such as sodium alginate. Additional excipients are, in particular, flow regulators and lubricants, for example salicylic acid, talc, stearic acid or salts thereof, such as magnesium stearate or calcium stearate, and/or polyethylene glycol, or derivatives thereof.

Coated tablet cores can be provided with suitable coatings which, if appropriate, are resistant to gastric juice, the coatings used being, inter alia, concentrated sugar solutions, which, if appropriate, comprise gum arabic, talc, polyvinylpyrrolidine, polyethylene glycol and/or titanium dioxide, coating solutions in suitable organic solvents or solvent mixtures or, for the preparation of coatings which are resistant to gastric juice, solutions of suitable cellulose preparations, such as acetylcellulose phthalate or hydroxypropylmethylcellulose phthalate.

By "controlled release" it is meant for purposes of the present invention that therapeutically active compound is released from the preparation at a controlled rate or at a specific site, for example, the intestine, or both such that therapeutically beneficial blood levels (but below toxic levels) are maintained over an extended period of time, e.g., providing a 12 hour or a 24 hour dosage form.

The term "rate controlling polymer" as used herein includes hydrophilic polymers, hydrophobic polymers or mixtures of hydrophilic and/or hydrophobic polymers that are capable of retarding the release of the compounds in vivo. In addition, many of the same polymers can be utilized to create an enteric coating of a drug, drug suspension, or drug matrix. It is within the skill of those in the art to modify the coating thickness, permeability, and dissolution characteristics to provide the desired controlled release profile (e.g., drug release rate and locus) without undue experimentation.

Examples of suitable controlled release polymers to be used in this invention include hydroxyalkylcellulose, such as hydroxypropylcellulose and hydroxypropylmethylcellulose; poly(ethylene)oxide; alkylcellulose such as ethycellulose and methylcellulose; carboxymethylcellulose; hydrophilic cellulose derivatives; polyethylene glycol; polyvinylpyrrolidone; cellulose acetate; cellulose acetate butyrate; cellulose acetate phthalate; cellulose acetate trimellitate; polyvinylacetate phthalate; hydroxypropylmethylcellulose phthalate; hydroxypropylmethylcellulose acetate succinate; poly(alkyl methacrylate); and poly (vinyl acetate). Other suitable hydrophobic polymers include polymers or copolymers derived from acrylic or methacrylic acid esters, copolymers of acrylic and methacrylic acid esters, zein, waxes, shellac and hydrogenated vegetable oils.

To ensure correct release kinetics, the controlled release preparation of this invention contains about 5 and 75% by weight, preferably about 20 and 50% by weight, more preferably about 30 to 45% by weight controlled release polymer(s) and about 1 to 40% by weight, preferably about 3 to 25% by weight active compounds. The controlled release preparation according to the invention can preferably include auxiliary agents, such as diluents, lubricants and/or melting binders. Preferably, the excipients are selected to minimize the water content of the preparation. Preferably, the preparation includes an antioxidant. Suitable diluents include pharmaceutically acceptable inert fillers such as microcrystalline cellulose, lactose, dibasic calcium phosphate, saccharides, and/or mixtures of any of the foregoing. The diluent is suitably a water soluble diluent. Examples of diluents include microcrystalline cellulose such as Avicel ph112, Avicel pH101 and Avicel pH102; lactose such as lactose monohydrate, lactose anhydrous, and Pharmatose DCL 21; dibasic calcium phosphate such as Emcompress; mannitol; starch; sorbitol; sucrose; and glucose. Diluents are carefully selected to match the specific formulation with attention paid to the compression properties. Suitable lubricants, including agents that act on the flowability of the powder to be compressed are, for example, colloidal silicon dioxide such as Aerosil 200; talc; stearic acid, magnesium stearate, and calcium stearate. Suitable low temperature melting binders include polyethylene glycols such as PEG 6000; cetostearyl alcohol; cetyl alcohol; polyoxyethylene alkyl ethers; polyoxyethylene castor oil derivatives; polyoxyethylene sorbitan fatty acid esters; polyoxyethylene stearates; poloxamers; and waxes.

To improve the stability in the controlled release preparation, an antioxidant compound can be included. Suitable antioxidants include sodium metabisulfite; tocopherols such as alpha, beta, or delta-tocopherol tocopherol esters and alpha-tocopherol acetate; ascorbic acid or a pharmaceutically acceptable salt thereof; ascorbyl palmitate; alkyl gallates such as propyl gallate, Tenox PG, Tenox s-1; sulphites or a pharmaceutically acceptable salt thereof; BHA; BHT; and monothioglycerol.

The controlled release preparation according to the invention preferably can be manufactured by blending the compounds with the controlled release polymer(s) and auxiliary excipients followed by direct compression. Other methods for manufacturing the preparation include melt granulation. Preferred melt granulation techniques include melt granulation together with the rate controlling polymer(s) and diluent(s) followed by compression of the granules and melt granulation with subsequent blending with the rate controlling polymer(s) and diluents followed by compression of the blend. As desired prior to compression, the blend and/or granulate can be screened and/or mixed with auxiliary agents until an easily flowable homogeneous mixture is obtained.

Oral dosage forms of the controlled release preparation according to the invention can be in the form of tablets, coated tablets, enterically coated tablets or can be multiparticulate, such as in the form of pellets or mini-tablets. If desired, capsules such as hard or soft gelatin capsules, can contain the multiparticulates. If desired, the multiparticulate oral dosage forms can comprise a blend of at least two populations of pellets or mini-tablets having different controlled-release in vitro and/or in vivo release profiles. If desired, one of the pellet or mini-tablet populations can comprise immediate release multiparticulate, such as multiparticulates formed by conventional means.

If desired, the controlled release matrix tablets or multiparticulates of this invention can be coated with a controlled release polymer layer so as to provide additional controlled release properties. Suitable polymers that can be used to form this controlled release layer include the rate controlling polymers listed above.

As desired, the tablets, pellets or mini-tablets according to the invention can be provided with a light-protective and/or cosmetic film coating, for example, film-formers, pigments, anti-adhesive agents and plasticizers. Such a film former may consist of fast-dissolving constituents, such as low-viscosity hydroxypropylmethylcelluose, for example Methocel E5 or D14 or Pharmacoat 606 (Shin-Etsu). The film coating may also contain excipients customary in film-coating procedures, such as light-protective pigments, for example iron oxide, or titanium dioxide, anti-adhesive agents, for example talc, and also suitable plasticizers such as PEG 400, PEG 6000, and diethyl phthalate or triethyl citrate.

The controlled release polymer of this invention may consist of a hydrogel matrix. For instance, the compounds can be compressed into a dosage form containing a rate controlling polymer, such as HPMC, or mixture of polymers which when wet will swell to form a hydrogel. The rate of release from this dosage form is controlled both by diffusion from the swollen tablet mass and by erosion of the tablet surface over time. The rate of release may be controlled both by the amount of polymer per tablet and by the inherent viscosities of the polymers used.

Dyes or pigments can be admixed to the tablets or coated tablet coatings, for example for identification or characterization of different doses of active ingredient.

Pharmaceutical compositions, which can be used orally, are also hard capsules of gelatin and soft, closed capsules of gelatin and a plasticizer, such as glycerol or sorbitol. The hard capsules can contain the active ingredient in the form of granules, mixed for example with fillers, such as maize starch, binders and/or lubricants, such as talc or magnesium stearate, and stabilizers if appropriate. In soft capsules, the active ingredient is preferably dissolved or suspended in suitable liquid excipients, such as greasy oils, paraffin oil or liquid polyethylene glycols or fatty acid esters of ethylene glycol or propylene glycol, it being likewise possible to add stabilizers and detergents, for example of the polyethylene sorbitan fatty acid ester type.

Other oral forms of administration are, for example, syrups prepared in the customary manner, which comprise the active ingredient, for example, in suspended form and in a concentration of about 5% to 20%, preferably about 10% or in a similar concentration which results in a suitable individual dose, for example, when 5 or 10 ml are measured out. Other forms are, for example, also pulverulent or liquid concentrates for preparing of shakes, for example in milk. Such concentrates can also be packed in unit dose quantities.

Pharmaceutical compositions, which can be used rectally, are, for example, suppositories that comprise a combination of the active ingredient with a suppository base. Suitable suppository bases are, for example, naturally occurring or synthetic triglycerides, paraffin hydrocarbons, polyethylene glycols or higher alkanols.

Compositions which are suitable for parenteral administration are aqueous solutions of an active ingredient in water-soluble form, for example of water-soluble salt, or aqueous injection suspensions, which comprise viscosity-increasing substances, for example sodium carboxymethylcellulose, sorbitol and/or dextran, and if appropriate stabilizers. The active ingredient can also be present here in the form of a lyophilisate, if appropriate together with excipients, and be dissolved before parenteral administration by addition of suitable solvents. Solutions such as are used, for example, for parental administration can also be used as infusion solutions. Preferred preservatives are, for example. Antioxidants, such as ascorbic acid, or microbicides, such as sorbic or benzoic acid.

Ointments are oil-in-water emulsions, which comprise not more than 70%, but preferably 20-50% of water or aqueous phase. The fatty phase consists, in particular, hydrocarbons, for example vaseline, paraffin oil or hard paraffin's, which preferably comprise suitable hydroxy compounds, such as fatty alcohol's or esters thereof, for example cetyl alcohol or wool wax alcohols, such as wool wax, to improve the water-binding capacity. Emulsifiers are corresponding lipophilic substances, such as sorbitan fatty acid esters (Spans), for example sorbitan oleate and/or sorbitan isostearate. Additives to the aqueous phase are, for example, humectants, such as polyalcohols, for example glycerol, propylene glycol, sorbitol and/or polyethylene glycol, or preservatives and odoriferous substances.

Fatty ointments are anhydrous and comprise, as the base, in particular, hydrocarbons, for example paraffin, vaseline or paraffin oil, and furthermore naturally occurring or semi-synthetic fats, for example hydrogenated coconut-fatty acid triglycerides, or, preferably, hydrogenated oils, for example hydrogenated groundnut or castor oil, and furthermore fatty acid partial esters of glycerol, for example glycerol mono- and/or distearate, and for example, the fatty alcohols. They also contain emulsifiers and/or additives mentioned in connection with the ointments which increase uptake of water.

Creams are oil-in-water emulsions, which comprise more than 50% of water. Oily bases used are, in particular, fatty alcohols, for example lauryl, cetyl or stearyl alcohols, fatty acids, for example palmitic or stearic acid, liquid to solid waxes, for example isopropyl myristate, wool wax or beeswax, and/or hydrocarbons, for example vaseline (petrolatum) or paraffin oil. Emulsifiers are surface-active substances with predominantly hydrophilic properties, such as corresponding nonionic emulsifiers, for example fatty acid esters of polyalcohols or ethyleneoxy adducts thereof, such as polyglyceric acid fatty acid esters or polyethylene sorbitan fatty esters (Tweens), and furthermore polyoxyethylene fatty alcohol ethers or polyoxyethylene fatty acid esters, or corresponding ionic emulsifiers, such as alkali metal salts of fatty alcohol sulfates, for example sodium lauryl sulfate, sodium cetyl sulfate or sodium stearyl sulfate, which are usually used in the presence of fatty alcohols, for example cetyl stearyl alcohol or stearyl alcohol. Additives to the aqueous phase are, inter alia, agents which prevent the creams from drying out, for example polyalcohols, such as glycerol, sorbitol, propylene glycol and/or polyethylene glycols, and furthermore preservatives and odoriferous substances.

Pastes are creams and ointments having secretion-absorbing powder constituents, such as metal oxides, for example titanium oxide or zinc oxide, and furthermore talc and/or aluminum silicates, which have the task of binding the moisture or secretions present.

Foams are administered from pressurized containers and they are liquid oil-in-water emulsions present in aerosol for. As the propellant gases, halogenated hydrocarbons, such as chlorofluoro-lower alkanes, for example dichlorofluoromethane and dichlorotetrafluoroethane, or, preferably, non-halogenated gaseous hydrocarbons, air, $N_2O$, or carbon dioxide are used. The oily phases used are, inter alia, those mentioned above for ointments and creams, and the additives mentioned there are likewise used.

Tinctures and solutions usually comprise an aqueous-ethanolic base to which, humectants for reducing evaporation, such as polyalcohols, for example glycerol, glycols and/or polyethylene glycol, and re-oiling substances, such as fatty acid esters with lower polyethylene glycols, i.e. lipophilic substances soluble in the aqueous mixture to substitute the fatty substances removed from the skin with the ethanol, and, if necessary, other excipients and additives, are admixed.

The invention also relates to a process or method for treatment of the disease states mentioned above. The compounds can be administered prophylactically or therapeutically as such or in the form of pharmaceutical compositions, preferably in an amount, which is effective against the diseases mentioned. With a warm-blooded animal, for example a human, requiring such treatment, the compounds are used, in particular, in the form of pharmaceutical composition. A daily dose of about 0.1 to about 5 g, preferably 0.5 g to about 2 g, of a compound of the present invention is administered here for a body weight of about 70 kg.

It is understood that the examples and embodiments described herein are for illustrative purposes only and that various substitutions, modifications or changes in light thereof will be suggested to persons skilled in the art and are included within the spirit and purview of this application and are considered within the scope of the appended claims. The following examples are given by way of example of the preferred embodiments, and are in no way considered to be limiting to the invention. For example, the relative quantities of the ingredients may be varied to achieve different desired effects, additional ingredients may be added, and/or similar ingredients may be substituted for one or more of the ingredients described. All publications, patents, and patent applications cited herein are hereby incorporated by reference in their entirety for all purposes.

Synthesis of the Compounds of the Invention (Refer to Table 3)

Mol-6 and Mol-7 ($Z=CH_2$)

The preparation process of the compounds of the invention comprises the implementation of known methods of peptide synthesis from gamma amino acids, said amino acids being N-protected by Fmoc or Boc. The synthesis method is the same as the one known for alpha-peptides.

The preparation of N-protected γ-amino acids is already described in prior art (Hintermann et al., *Helv. Chim. Acta* 1998, 41, 983-1002).

According to an advantageous embodiment of the invention, the γ-amino acids are prepared according to Smrcina et al., *Tetrahedron*, 1997, 53, 12867-12874).

The N-Boc-protected γ-amino acids used for the implementation of the process of the invention are produced from the corresponding natural α-amino acids. The amino acid is first transformed by acylation with Meldrum acid in presence of carbodiimide (example: EDC) and 4-dimethylamino pyridine. After reduction with $NaBH_4$, in a mixture of dichloromethane and acetic acid, the compound as obtained is cyclized in pyrrolidone in toluene at 110° C. for 4 hours. After the opening of the cycle in basic medium (NaOH in MeOH), the γ-amino acids are obtained with yields comprised from 15 to 60%.

The preferred γ-amino acids are the following:

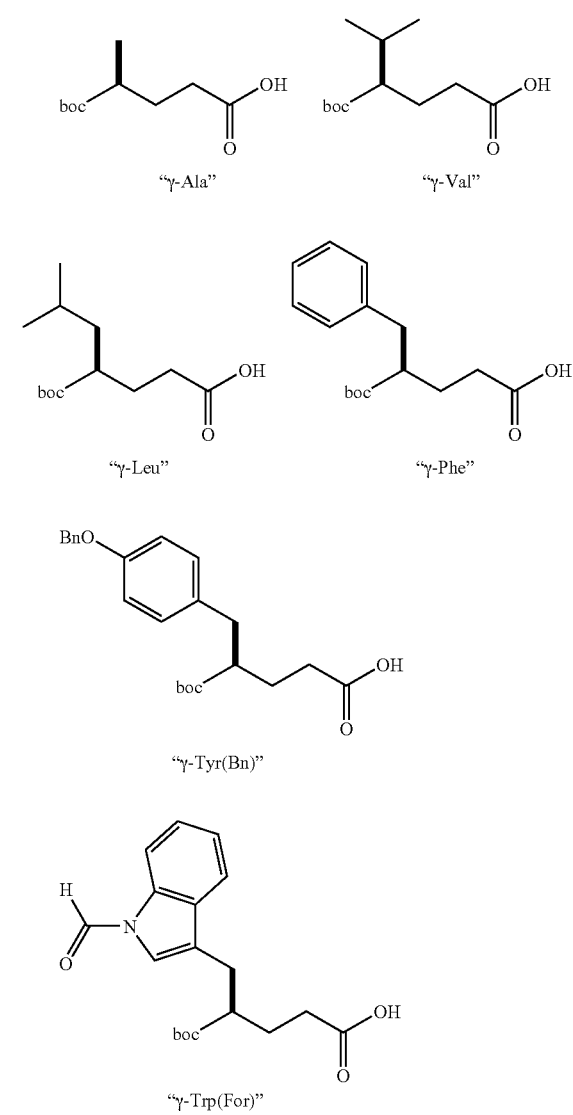

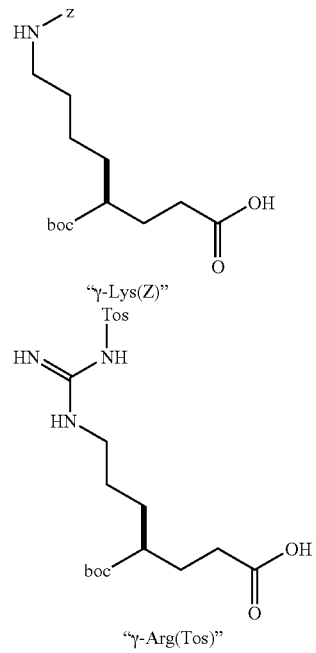

The assembling of the peptide chain is then carried out with a peptides synthesizer in semi-automatic mode on a MBHA (4-methylbenzhydrylamine) resin of polystyrene type and on a scale of 25 micromole. The N-Boc-protected γ-amino acids (3 equiv) are used instead of standard Boc-amino acids and they are incorporated by using the classic coupling procedure with a mixture of BOP (benzotriazol-1-yloxy-tris (dimethylamino)phosphonium hexafluorophosphate)/HOBt (1-hydroxybenzotriazole)(3 equiv/3 equiv) in presence of diisopropylethylamine (12 equiv) in order to carry out the in situ neutralisation. A double coupling is systematically carried out. The end of the coupling reaction is checked out by a Kaiser test with ninhydrine. At the end of the synthesis, the resin is washed with dichloromethane, and ether, and it is dried under vacuum. The peptide/resin is then cleaved by a treatment with HF (hydrofluoric acid) for an hour and the peptide is precipitated with ether to give the crude peptide, which is then purified with HPLC and lyophilised. The identity of each peptide is controlled by mass spectrometry. The purity of synthesized peptides is greater than 94% on the basis of HPLC analysis on a inverse phase column of type C18 and by using a mixture water/acetonitrile.

Mol-1, Mol-2, Mol-3, Mol-4, and Mol-5 (Z=NH)

The assembling of the peptide chain is carried out with a peptides synthesizer in semi-automatic mode on a MBHA resin of polystyrene type and on a scale of 25 micromole. The N-Boc-protected γ-amino acids (3 equiv) are incorporated by using the classic coupling procedure with a mixture BOP/HOBt (3 equiv/3 equiv) in presence of diisopropylethylamine (12 equiv) in order to carry out the in situ neutralisation. A double coupling is systematically carried out. The end of the coupling reaction is checked out by a Kaiser test with ninhydrine. The Boc group is eliminated after the coupling by a treatment with TFA (trifluoroacetic acid).

The following monomers are succinimidyl or paranitrophenyl carbamates which are derived of protected diamines prepared according to (1)—Kim, J. M.; Bi, Y.; Paikoff, S. J.; Schultz, P. G., *Tetrahedron Lett*., (1996) 37, 5305, (2)—Boeijen, A., van Ameijde, J.; Liskamp, R. M. J., *J. Org. Chem.*, (2001), 66, 8454 and (3)—Guichard, G.; Semetey, V.; Didierjean, C.; Aubry, A.; Briand, J.-P.; Rodriguez, M., *J. Org. Chem.*, (1999) 64, 8702.

The coupling of these monomers is generally carried out in DMF (dimethylformamide)(4 equiv, 2×2 hours in DIEA (diisopropylethylamine)(4 equiv)). After deprotection of the last Boc group, the resin is treated with isopropyl isocyanate in the same conditions.

At the end of the synthesis, the resin is washed with dichloromethane, and ether, and it is dried under vacuum. The peptide/resin is then cleaved by a treatment with HF for an hour and the peptide is precipitated with ether to give the crude oligomers Mol-1 to Mol-5, which are then purified with HPLC and lyophilised. The identity of each peptide is controlled by mass spectrometry. The purity of synthesized peptides is greater than 94% on the basis of HPLC analysis on a inverse phase column of type C18 and by using a mixture water/acetonitrile.

For the compounds of the invention wherein Z=O, the monomers GP-D$^t$-W are prepared according to Cho, C. Y.; Youngquist, R. S.; Paikoff, S. J.; Beresini, M. H.; Hebert, A. R.; Berleau, L. T.; Liu, C. W.; Wemmer, D. E.; Keough, T.; Schultz, P. G.; *J. Am. Chem. Soc.* (1998) 120(31); 7706-7718.

In Vitro Susceptibility of Aerobic Bacteria

Material and Method

Four strains were selected: *Escherichia Coli* ATCC 25922, *Staphylococcus Aureus* ATCC 25923, *Pseudomonas Aeruginosa* ATCC 27853 and a clinical isolated methicillin resistant *Staphylococcus Aureus* strain. Antibacterial activity of the molecules was tested by dilution method in Mueller-Hinton broth in order to determine the minimal inhibitory concentration (MIC) and the minimal bactericidal concentration (MBC). At least two independent assays were done. Stock solutions were obtained by solubilizing molecule powders in distilled water at concentration of 2.56 mg/mL and serial 2-fold diluted solutions were prepared. Bacterial inoculum was standardized by using direct suspensions of colonies from overnight growth in saline adjusted to a turbidity matching the 0.5 McFarland standard, and diluted to obtain a density comprised between $10^5$ CFU/mL and $10^7$ CFU/mL. Tubes containing 900 μL of inoculum with 100 μL of molecules solutions were incubated in air at 37° C. for 18 to 20 hours. Purity and inoculum density as well as percentage of viable bacteria in limpid tubes were checked by plate counting on sheep blood agar. Broth not containing any molecule solution was inoculated with each selected bacterial strain as a control for organism viability (growth control). The susceptibility of *S. Aureus* strains against vancomycin was used as an internal control as well as the activity of melittin.

TABLE 1

| Minimal inhibitory concentration (μg/ml). | | | | |
|---|---|---|---|---|
| | *Escherichia Coli* ATCC 25922 | *Staphylococcus Aureus* ATCC | *Pseudomonas Aeruginosa* ATCC 27853 | clinical isolated methicillin resistant *Staphylococcus Aureus* strain |
| Mol-4 | 32 | 8 | 128 | 16 |
| Mol-8 | 32 | 32 | 64 | Not tested |
| vancomycin | Not tested | 2 | Not tested | 1 |
| mellitin | >256 | 32 | >256 | 32 |

TABLE 2

| Minimal bactericidal concentration (μg/ml). | | | | |
|---|---|---|---|---|
| | *Escherichia Coli* ATCC 25922 | *Staphylococcus Aureus* ATCC | *Pseudomonas Aeruginosa* ATCC 27853 | clinical isolated methicillin resistant *Staphylococcus Aureus* strain |
| Mol-4 | 64 | <16 | 256 | 64 |
| Mol-8 | 256 | 32 | >256 | Not tested |
| vancomycin | Not tested | Not tested | Not tested | Not tested |
| mellitin | >256 | 128 | >256 | 128 |

Mol-8 is a urea oligomer of formula:

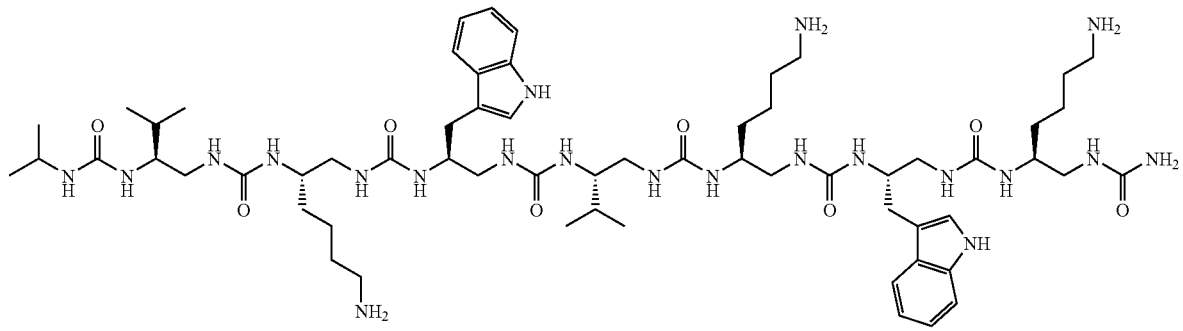

These results show that hybrid oligomer Mol-4 is more potent than corresponding urea oligomer Mol-8. Thus, these results show that the insertion on C-terminus of γ-amino acid residue is important to increase the potency of the antibacterial compounds. While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

TABLE 3
Example Oligomeric Compounds of the Invention.
| Compound No. | CHEMICAL FORMULA |
|---|---|
| Mol-1 | 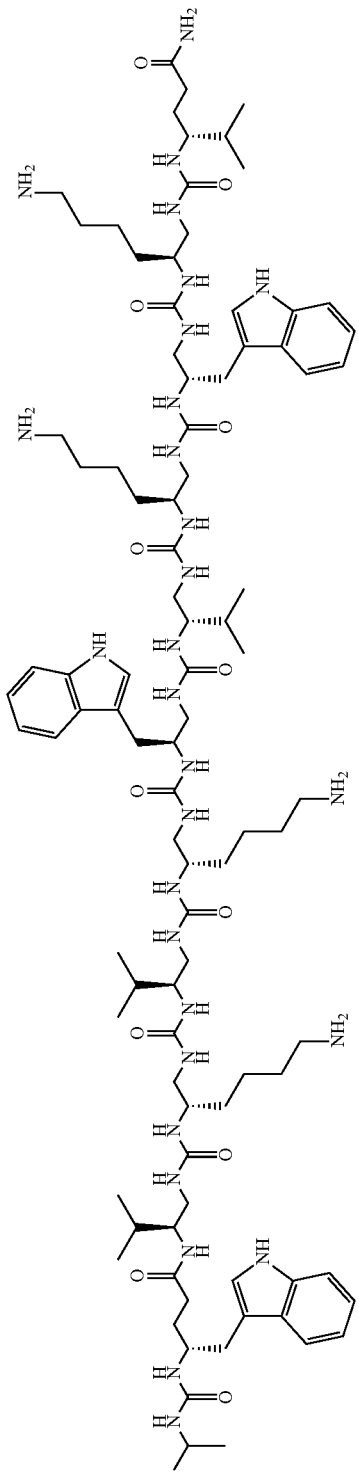 |
| Mol-2 | 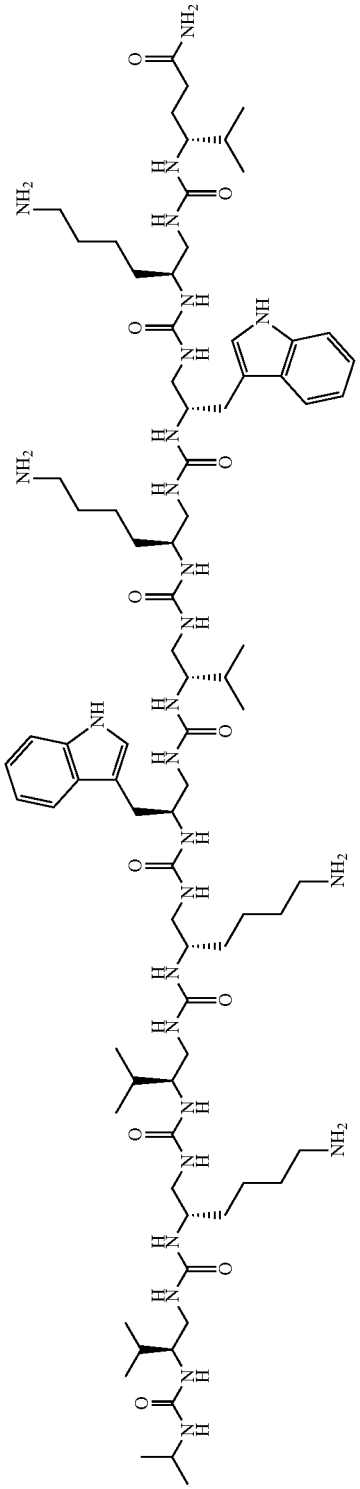 |

TABLE 3-continued
Example Oligomeric Compounds of the Invention.
| Compound No. | CHEMICAL FORMULA |
|---|---|
| Mol-3 | 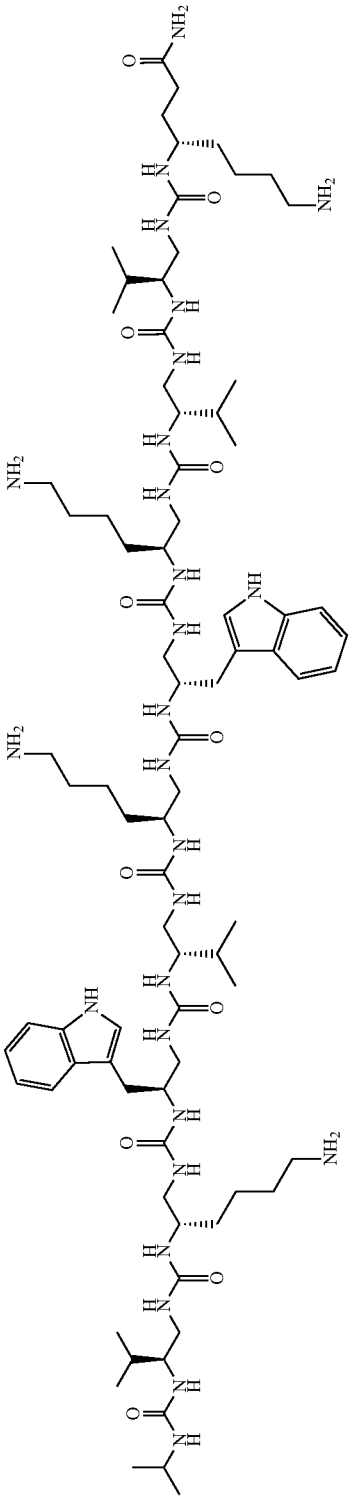 |
| Mol-4 | 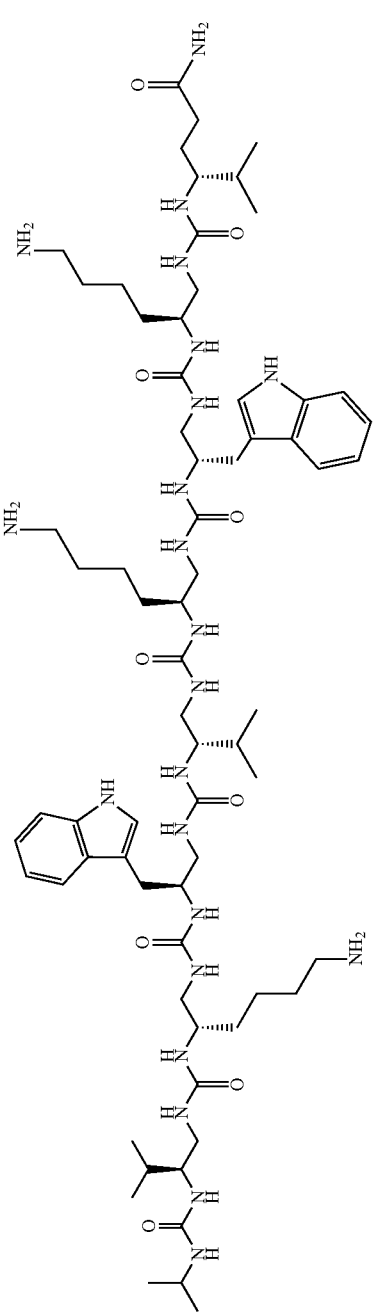 |

TABLE 3-continued
Example Oligomeric Compounds of the Invention.
| Compound No. | CHEMICAL FORMULA |
|---|---|
| Mol-5 | 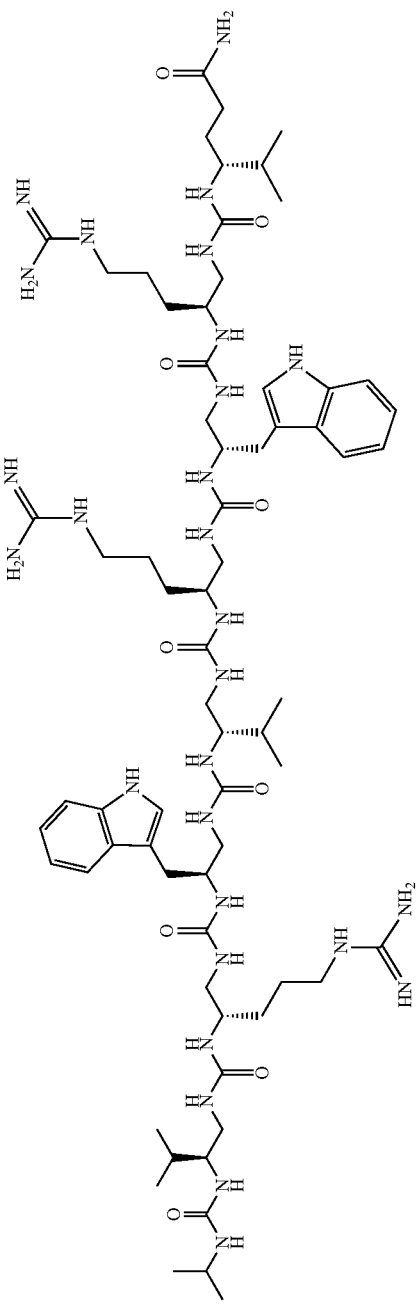 |
| Mol-6 | 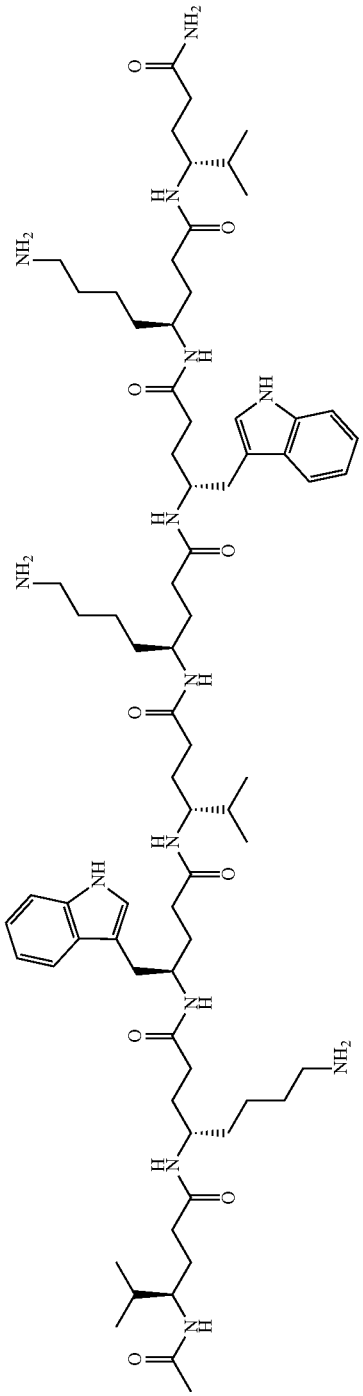 |

TABLE 3-continued
Example Oligomeric Compounds of the Invention.
| Compound No. | CHEMICAL FORMULA |
|---|---|
| Mol-7 | 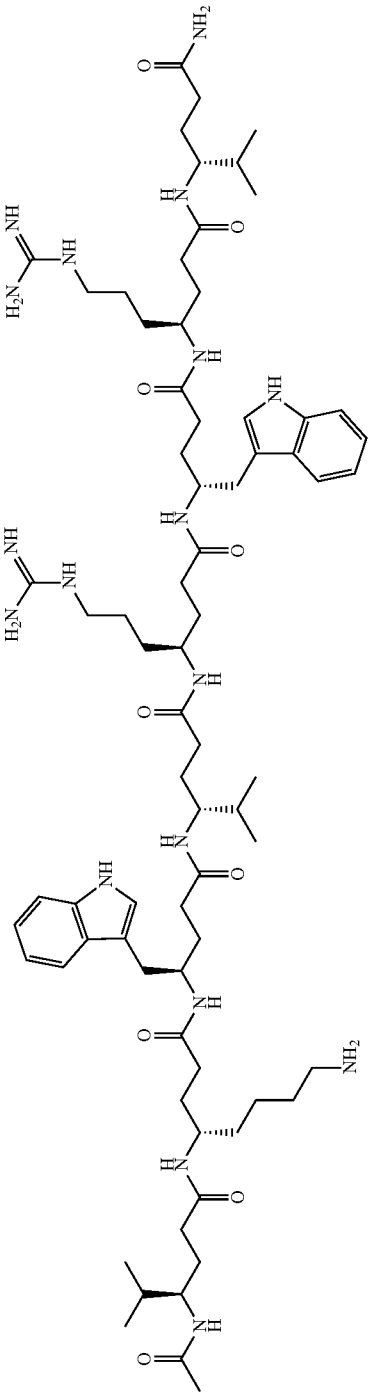 |
| Mol-8 | 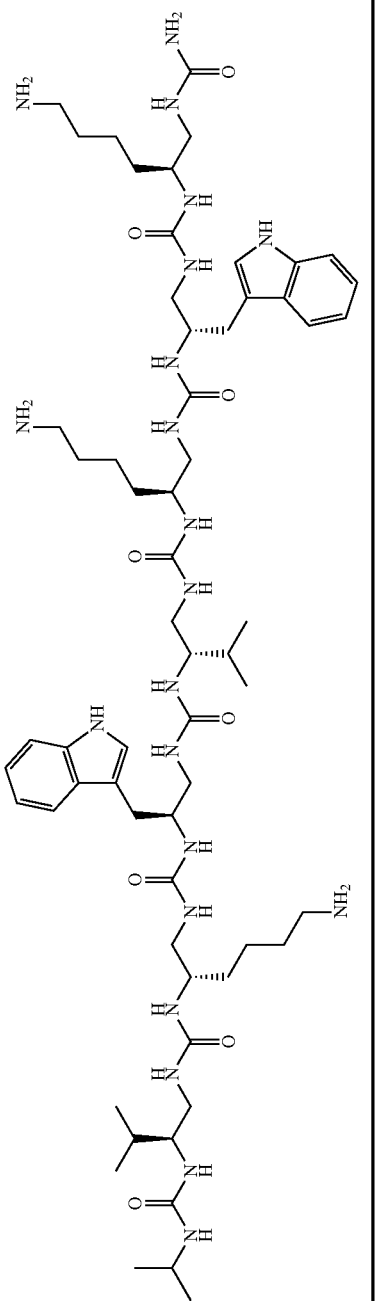 |

The invention claimed is:

1. An oligomeric compound of formula I:

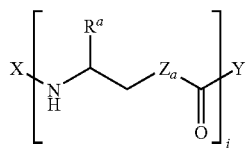

wherein i is an integer varying from 7 to 9;

wherein $R^a$ is a member independently selected from the group consisting of a hydrogen atom, an amino acid side chain, a ($C_1$-$C_{10}$) alkyl, and ($C_1$-$C_{10}$) bicyclic heteroaryl group comprising up to 5 N groups optionally substituted by 1 to 6 substituents further selected from the group consisting of: amidine, ($C_1$-$C_{10}$) alkyl, or $NH_2$, wherein $Z_a$ is $CH_2$ or NH;

wherein X is selected from the group consisting of a

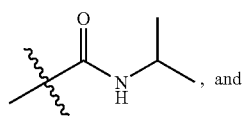, and

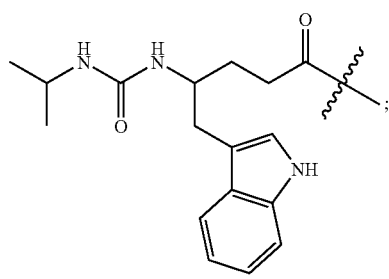;

wherein Y represents $NH_2$, or a group chosen among the following:

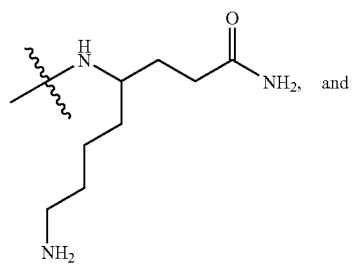, and

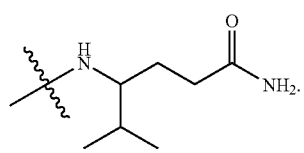.

2. The oligomeric compounds of claim 1, wherein at least 30% to 50% of the groups $R^a$ comprise

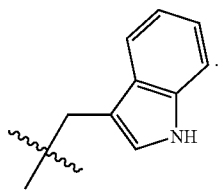

3. The oligomeric compound of claim 1, wherein i=8.

4. The oligomeric compound of claim 1, wherein said compound is present in combination with a pharmaceutically acceptable excipient.

5. The oligomeric compound of claim 4, wherein the combination comprises a per unit dose of from about 10 to about 2000 mg of a compound of claim 1.

6. A pharmaceutical compound comprising the oligomeric compound of claim 1 conjugated to a pharmacologically active molecule.

7. The pharmaceutical compound of claim 6, wherein the pharmacologically active molecule is conjugated to a terminus of the oligomeric compound.

8. A medicament for the treatment of bacterial, or fungal diseases, and in particular fungal infections such as aspergillosis and candidosis, and resistant bacterial infections comprising an effective amount of the oligomeric compound of claim 1.

9. The oligomeric compound of claim 1, wherein i=7.

10. The oligomeric compound of claim 1, wherein i=9.

11. The ologomeric compound of claim 1, wherein $R^a$ is a member selected from the group consisting of a

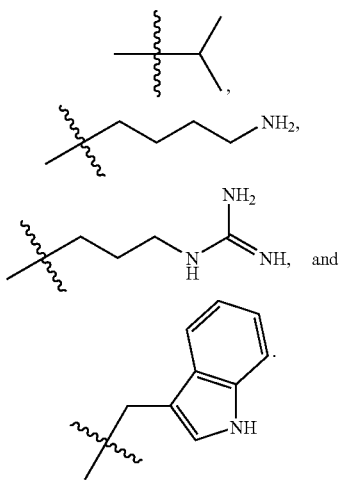

12. The oligomeric compound of claim 1, wherein i=7 and $Z_a$ is NH.

13. The oligomeric compound of claim 1, wherein i=8 and $Z_a$ is $CH_2$.

14. The oligomeric compound of claim 1, wherein i=9 and $Z_a$ is NH.

15. The oligomeric compound of claim 1, having the formula of Mol-1:

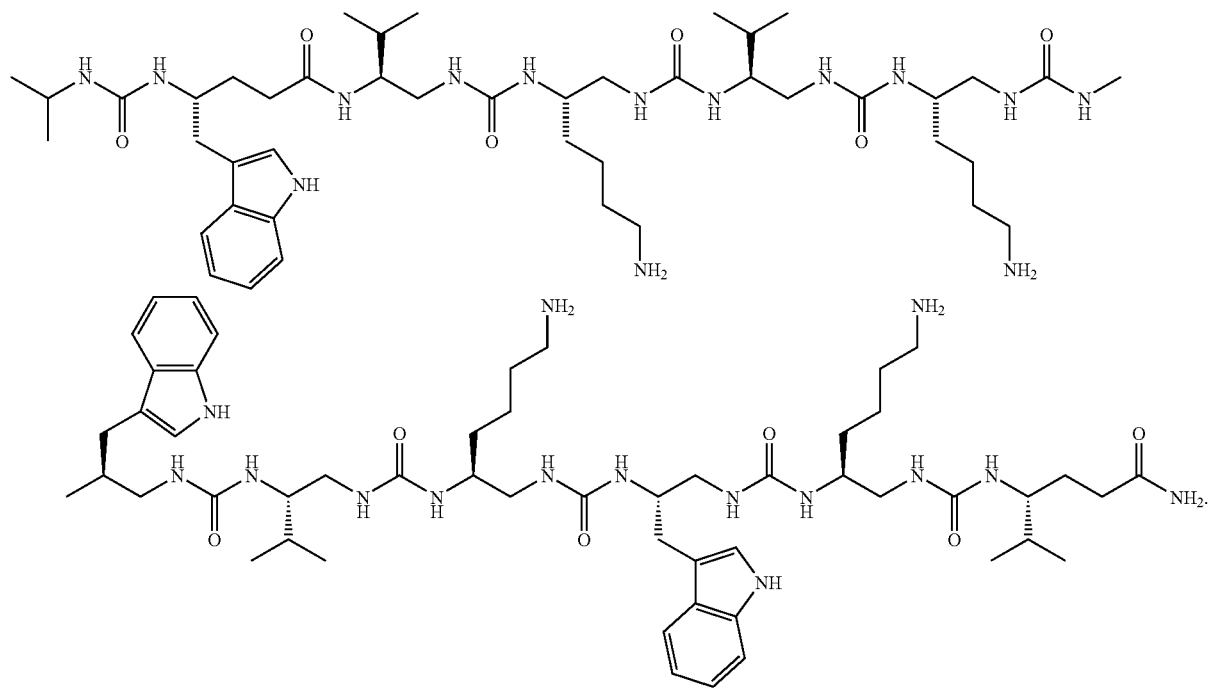
16. The oligomeric compound of claim 1, having the formula of Mol-2:
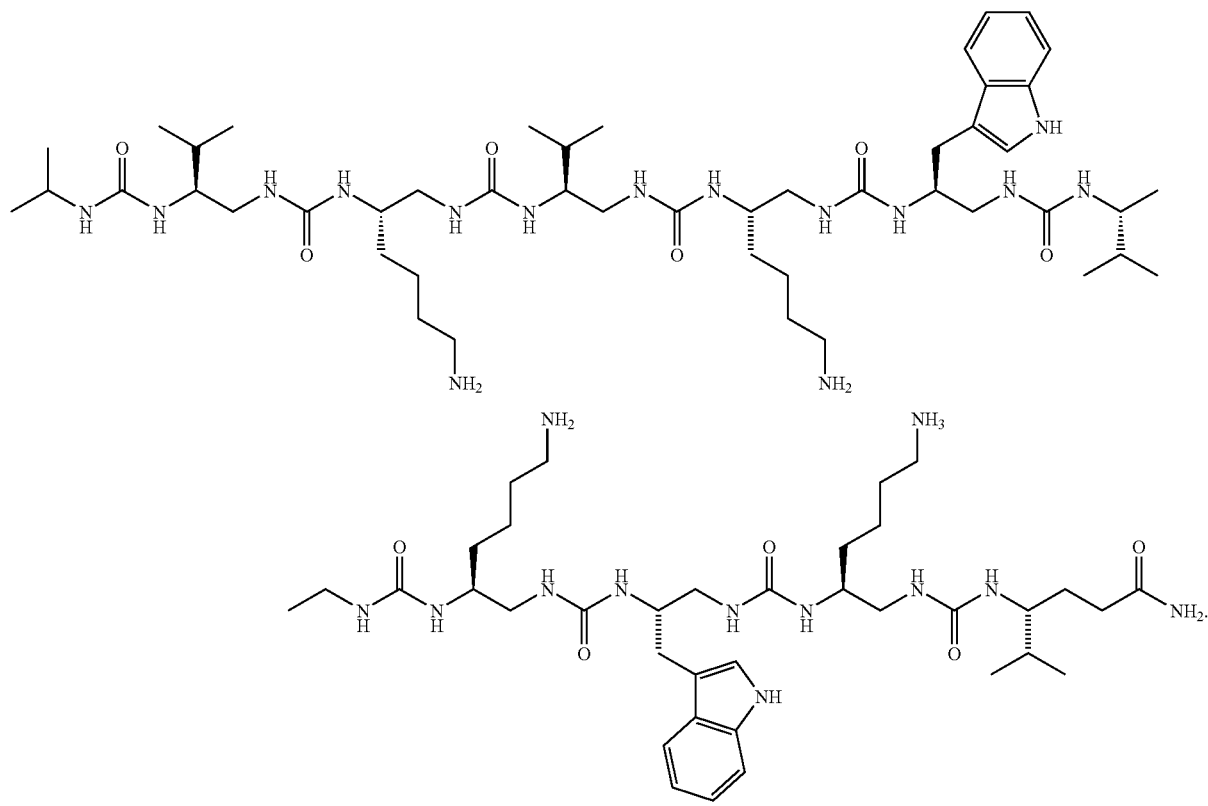

17. The oligomeric compound of claim 1, having the formula Mol-3:
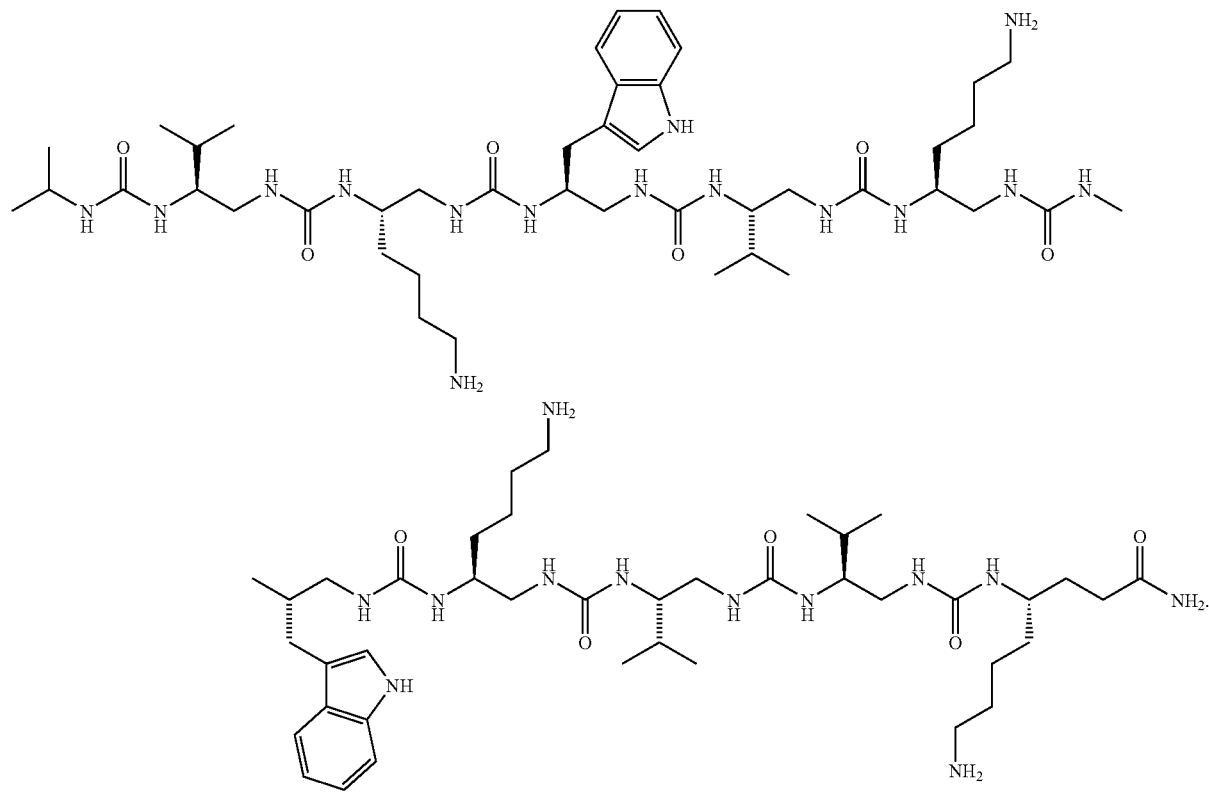
18. The oligomeric compound of claim 1, having the formula Mol-4:
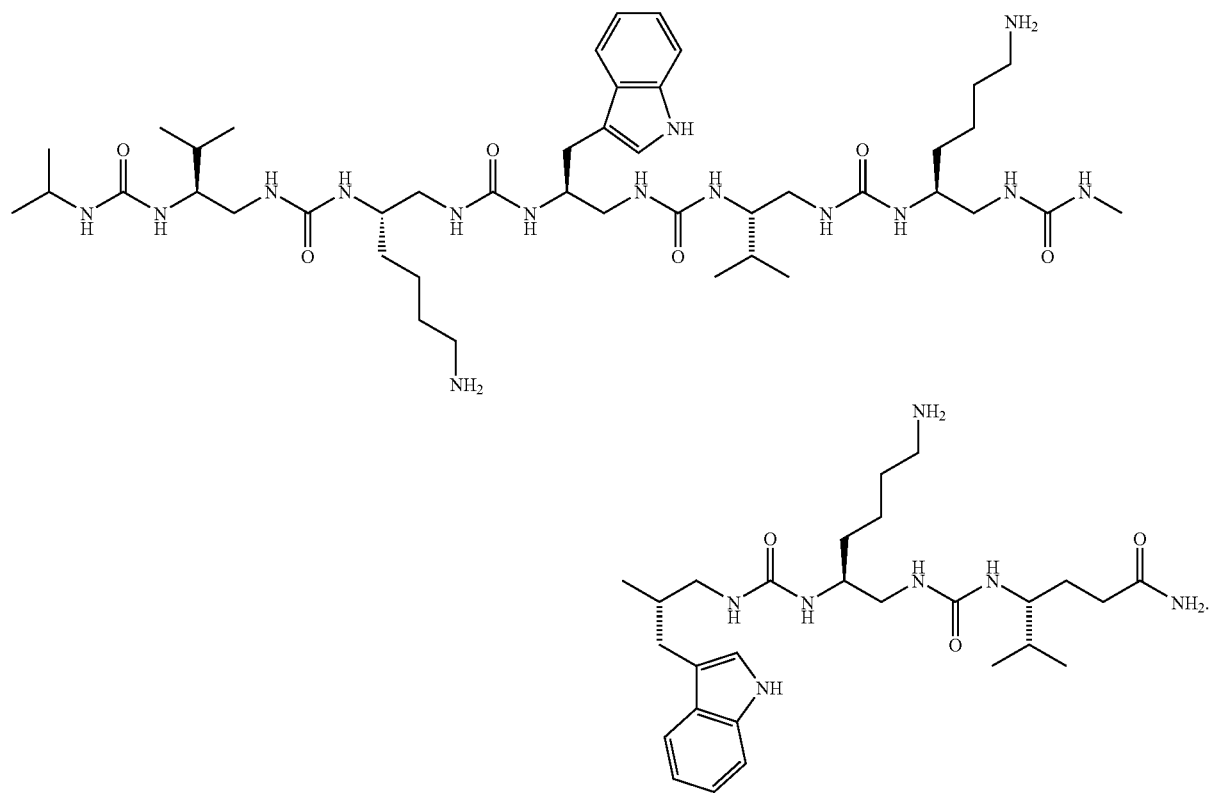

19. The oligomeric compound of claim 1, having the formula Mol-5:
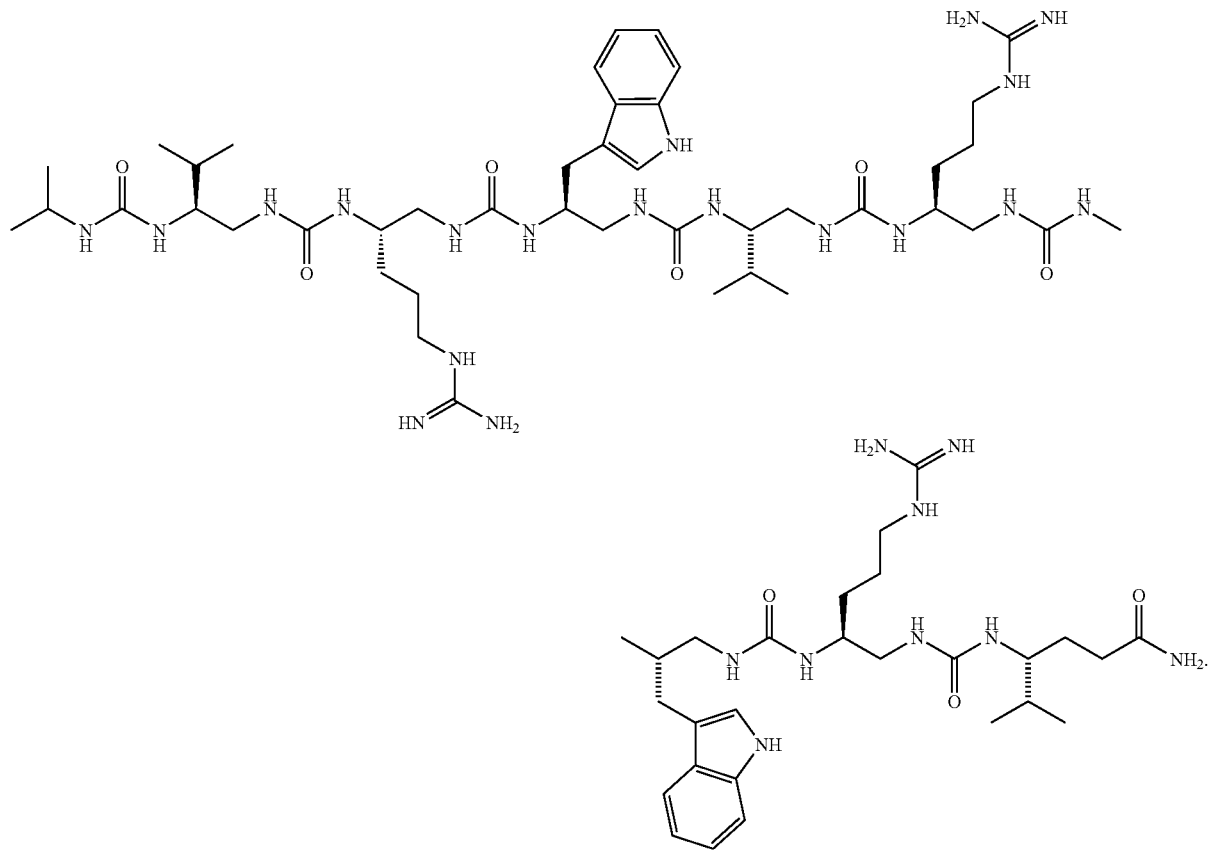
20. The oligomeric compound of claim 1, having the formula Mol-6:
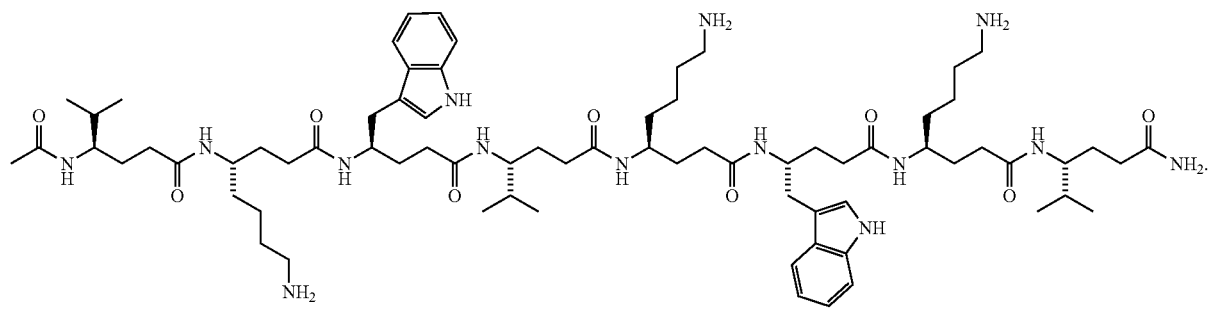
21. The oligomeric compound of claim 1, having the formula Mol-7:
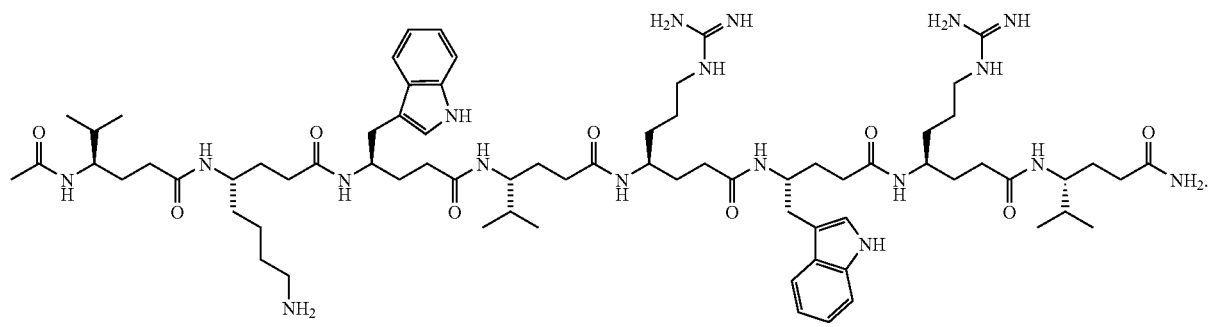

22. The oligomeric compound of claim 1, having the formula of Mol-8:

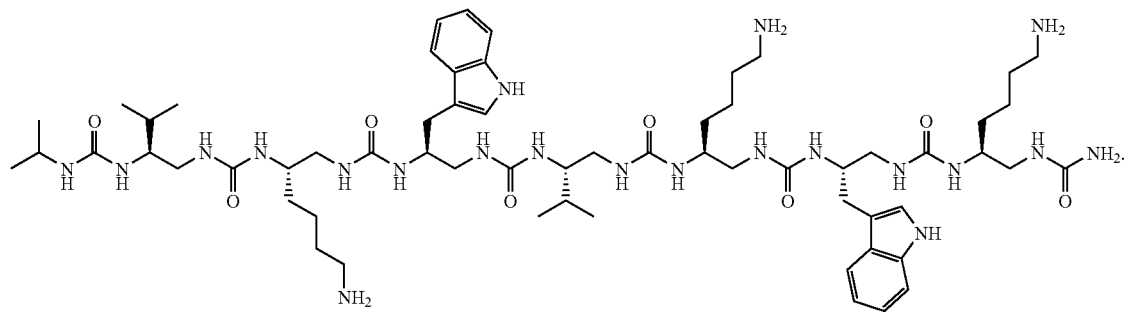

23. A method for the treatment of disease in an individual comprising:
    providing a composition comprising the oligomeric compound of claim 1 and a pharmaceutically acceptable carrier, and administering an effective amount of said oligomeric compound in a pharmaceutically acceptable form to an individual, wherein the individual suffers from a fungal infection, bacterial infection, or a combination thereof.

24. The method of claim 23, wherein the fungal infection comprises aspergillosis and candidosis.

25. A process for the preparation of an oligomeric compounds of claim 1, comprising:
    (a) preactivating monomers of formula GP-D-W, wherein GP is a protective group selected from the group consisting of Fmoc, Teoc, phtalimide, Alloc, BOC and Cbz; D is

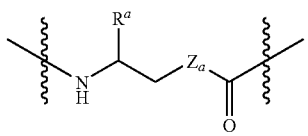

wherein $R^a$ and $Z_a$ are as defined in claim 1, W is OH or is a member selected from the W-H group consisting of N-hydroxysuccinimide, phenol, pentafluorophenol, pentachlorophenol, p-nitrophenol, 2,4-dinitrophenol, 2,4,5-trichlorophenol, 2,4-dichloro-6-nitrophenol, hydroxy-1,2,3,-benzotriazole, 1-oxo-2-hydroxydihydrobenzo-triazine (HODhbt), 7-aza-1-hydroxy-benzotriazole (HOAt), 4-aza-1-hydroxybenzo-triazole (4-HOAt), imidazole, tetrazole, and WANG resin;
    (b) coupling of GP-D-W as defined above on an amine function of a support, wherein the coupling allows the grafting of the -D-GP group to said amine function of said support;
    (c) cleaving of the GP group;
    (d) repeating of steps (a) and (b) until n D groups have been added to the grafted group(s), wherein the new -D-GP group(s) is added to the previously grafted group(s), wherein n is as defined in claim 1,
    (e) adding the X group as defined in claim 1 to the grafted groups; and
    (f) cleaving of the compound of formula (I) from the support, which allows the removal of the resin and the release of the Y group, as defined in claim 1.

26. The process of claim 25, wherein step (b) is carried out in the presence of a tertiary base selected from the group consisting of DIEA, collidine, NMM and lutidine; and in the presence of a catalyst.

27. The process of claim 26, wherein said catalyst is HOBt.

28. The process of claim 25, wherein step (b) is carried out in a solvent selected from the group consisting of DMF, $CH_2Cl_2$, THF, and N-methylpyrrolidone.

* * * * *